United States Patent
Pech et al.

(10) Patent No.: US 9,125,701 B2
(45) Date of Patent: Sep. 8, 2015

(54) SUBTALAR IMPLANT

(71) Applicant: ZIMMER GMBH, Winterthur (CH)

(72) Inventors: Uwe Pech, Tuttlingen (DE); Vladko Kotuljac, Schoemberg (DE)

(73) Assignee: Zimmer GmbH, Winterthur (CH)

( * ) Notice: Subject to any disclaimer, the term of this patent is extended or adjusted under 35 U.S.C. 154(b) by 100 days.

(21) Appl. No.: 13/649,148

(22) Filed: Oct. 11, 2012

(65) Prior Publication Data
US 2014/0107713 A1    Apr. 17, 2014

(51) Int. Cl.
*A61B 17/68* (2006.01)
*A61B 17/84* (2006.01)

(52) U.S. Cl.
CPC .............. *A61B 17/844* (2013.01); *A61B 17/68* (2013.01)

(58) Field of Classification Search
CPC .............. A61F 2/42; A61F 2002/4207; A61B 17/7258; A61B 17/7266; A61B 17/7275
USPC ......... 606/300, 301, 304, 305, 306, 309, 313; 623/16.11, 18.11, 21.11; 411/57.1, 411/60.1–60.3, 55
See application file for complete search history.

(56) References Cited

U.S. PATENT DOCUMENTS

| | | | |
|---|---|---|---|
| 2,435,876 A * | 2/1948 | De Swart | 411/55 |
| 5,360,450 A | 11/1994 | Giannini | |
| 5,554,191 A * | 9/1996 | Lahille et al. | 623/17.11 |
| 6,136,032 A * | 10/2000 | Viladot Perice et al. | 623/21.18 |
| 7,678,153 B2 | 3/2010 | Katz et al. | |
| 8,398,691 B2 * | 3/2013 | Viladot Perice et al. | 606/327 |
| 8,435,299 B2 | 5/2013 | Chauvin et al. | |
| 2002/0040243 A1 | 4/2002 | Attali et al. | |
| 2005/0251264 A1 | 11/2005 | Katz et al. | |
| 2011/0071579 A1 | 3/2011 | Reach, Jr. | |

FOREIGN PATENT DOCUMENTS

| | | |
|---|---|---|
| EP | 0560249 A1 | 9/1993 |
| EP | 1728491 A1 | 12/2006 |

OTHER PUBLICATIONS

International Search report dated Dec. 13, 2012.

* cited by examiner

*Primary Examiner* — Anu Ramana
(74) *Attorney, Agent, or Firm* — Schwegman Lundberg & Woessner, P.A.

(57) ABSTRACT

A subtalar implant (1) for stabilizing the subtalar joint in the human foot includes a longitudinal axis (L) extending between a front end (13) and a rear end (14), wherein a first anchor portion (2) is arranged to the side of the longitudinal axis (L) and a second anchor portion (3) is arranged to the side of the longitudinal axis (L). In accordance with the invention, a spreading mechanism (5) to spread apart the implant as a result of relative displacement of the first and second anchor portion (2, 3) at an angle to the longitudinal axis (L) are provided.

15 Claims, 2 Drawing Sheets

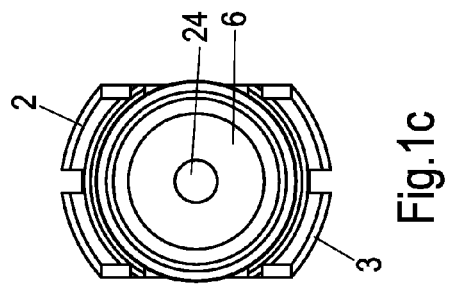
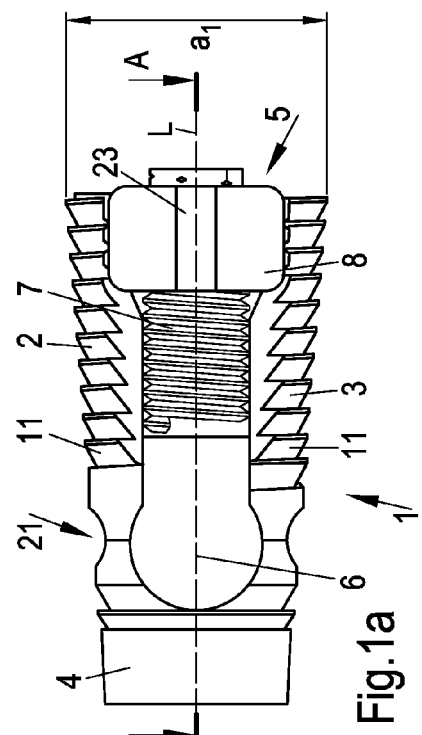
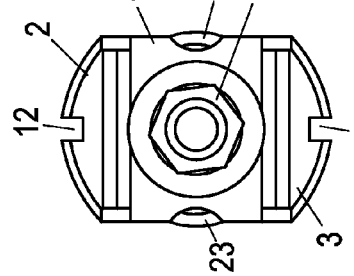
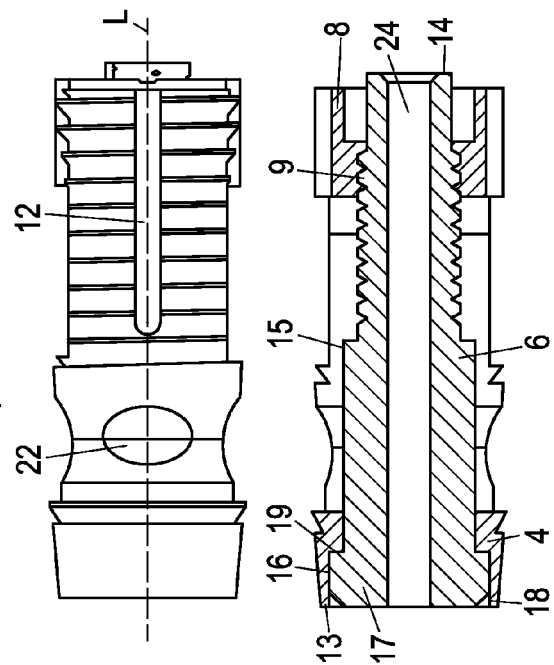

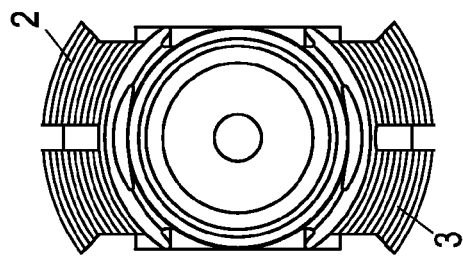
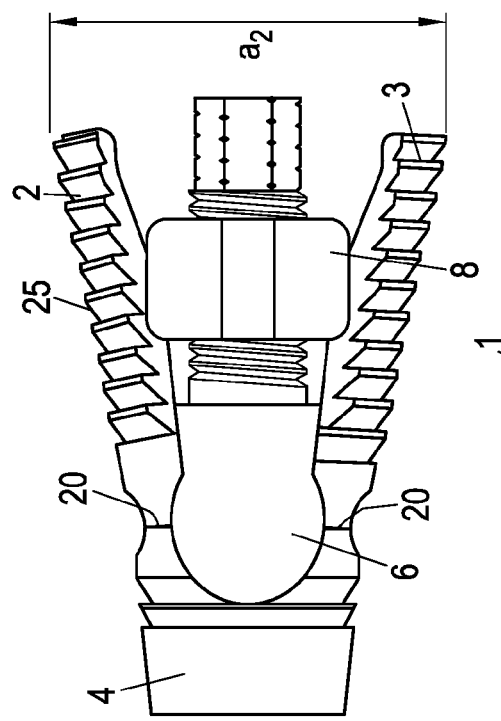
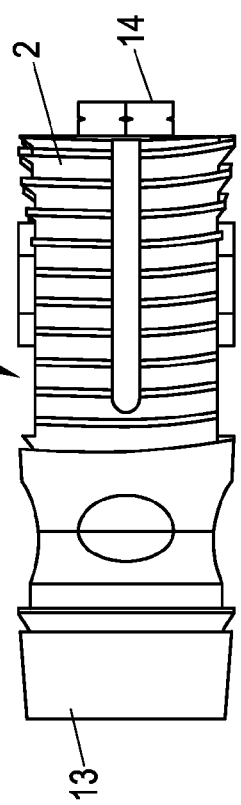
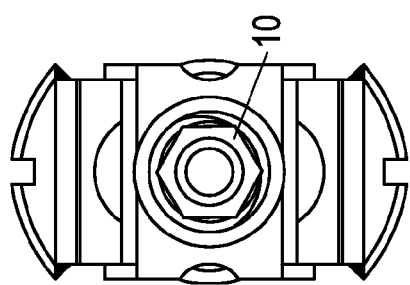

SUBTALAR IMPLANT

BACKGROUND OF THE INVENTION

The invention relates to a subtalar implant according to the preamble of Claim 1 for stabilising the subtalar joint in the human foot, comprising a (virtual) longitudinal axis extending between a front end and a rear end, comprising a first anchor portion arranged to the side of the longitudinal axis and a second anchor portion arranged to the side of the longitudinal axis.

For treatment of flatfeet, it is known to screw in a subtalar implant between the calcaneus and talus when carrying out an operation to stabilise the subtalar joint in the human foot. Subtalar implants known from practice are formed in one piece, have a continuous channel for receiving a Kirschner wire and have a fixed conical sleeve contour, which is structured with a thread on the lateral surface so as to anchor the implant in the calcaneus and in the talus. Subtalar implants are provided in various sizes, from which the surgeon must choose a suitable (fitting) subtalar implant during the operation, wherein it may be that the selected implant does not fit optimally, and therefore has to be removed again and replaced by a more suitable subtalar implant.

SUMMARY OF THE INVENTION

Proceeding from the above-mentioned prior art, the object of the invention is to disclose an improved subtalar implant, which facilitates the operation (and preferably accelerates it), for stabilising the subtalar joint in the human foot, in particular for the treatment of flatfeet. The risk of errors during the operation is to be reduced. In addition, the need to store a large number of implants of different size is to be eradicated.

In the case of a generic subtalar implant, this object is achieved in particular by a subtalar implant having the features disclosed herein such in that the subtalar implant is provided with spreading means to spread apart the implant as a result of relative displacement of the first and second anchor portion at an angle to the longitudinal axis.

Advantageous developments of the invention are also disclosed. All combinations of at least two features disclosed in the description, the claims and/or the figures fall within the scope of the invention.

The invention is based on the concept of designing the subtalar implant so as to be expandable, that is to say spreadable, so as to thus be able to adjust the radial extension of the subtalar implant during the operation, in particular from the anchor portions thereof, based on the longitudinal axis. To this end, the subtalar implant is assigned integral spreading means so as to adjust an angle (angle of spread) spanned between the at least two anchor portions. As a result of the embodiment according to the invention of the subtalar implant, it is thus possible to dispense with the selection from a large number of rigid or unadjustable subtalar implants, in practice normally eight subtalar implants. The possibility for selection can at least be reduced in the event of provision of a plurality of subtalar implants having different spreading widths or ranges. On the whole, the length of the operation can be reduced by the subtalar implant according to the invention and the risk of incorrect selection can, at least, be considerably reduced due to the possibility to adapt the radial extension and due to the small number of different implants differing by the maximal and/or minimal spreading widths, and can be completely eliminated in particular if just one implant is provided. The subtalar implant according to the invention is suitable for the treatment of flatfeet, in particular in children.

It is most preferable if the anchor portions, with which the subtalar implant can be fixed in the sinus tarsi tunnel or anchored in bone, in particular in the calcaneus and in the talus, are components of a (virtual) conical sleeve contour of the subtalar implant, wherein, in this case, the adjustable angle of spread preferably corresponds to the cone angle of this sleeve contour. This may be adjustable in stages or preferably continuously, depending on the design of the spreading means.

The at least two anchor portions are preferably spaced from one another in the circumferential direction, at least when spread apart. It is particularly expedient if the anchor portions each extend over just a portion of the circumference of the subtalar implant. It has been found to be particularly expedient if, in particular when just two anchor portions are provided, each anchor portion extends over an angle at the circumference between approximately 60° and approximately 120°. It is particularly expedient if the circumferential extension of each anchor portion is approximately 90°.

If a total of two anchor portions that are adjustable relative to one another or can be spread apart from one another are provided, it is preferable if these are arranged diametrically opposed based on the virtual longitudinal axis. If more than two anchor portions are provided, these are distributed in the circumferential direction, wherein it is particularly preferable if the anchor portions are distributed uniformly in the circumferential direction.

So as to enable correct positioning of the subtalar implant between two bones in the foot during the operation, an axial continuous channel is provided in a development of the invention and extends between the front and the rear end of the subtalar implant, the continuous channel being designed and intended to receive a Kirschner wire. If the spreading means is designed as a spindle drive, as will be explained in greater detail further below, it is particularly expedient if the continuous channel passes centrally through a central, rotatably arranged, or alternatively rotationally fixed, spindle.

As explained in the introduction, the at least two anchor portions are used to hold the subtalar implant securely in human bone, to which end the anchor portions have to be lodged (anchored) into the bones. To this end, the anchor portions are provided on their outer surface with a surface structure so as to be able to lodge the subtalar implant some way into bone, for example by hammering it in, screwing it in and/or by the spreading process. It is particularly expedient if an outer thread is provided on the anchor portions, wherein this outer thread extends over the anchor portions or if the individual structured surfaces form part of a common outer thread. Alternatively, it is also conceivable to provide a grooved structure for example, wherein anchor portions structured in this way are buried in the bone, preferably by being hammered in and/or spread apart. It is particularly expedient if the surface structure is hook-like, in any case so that unintentional adjustment against a direction of introduction is reliably prevented.

With regard to the possibility of effective sterilisation and simple mechanical construction, it has proven to be advantageous if at least two of the anchor portions, in particular all anchor portions, are produced in one piece together with a connection portion (base portion) connecting said anchor portions, that is to say if said anchor portions are produced cohesively from a material piece (that is to say not in a number of parts). The base portion preferably simultaneously forms a holder for the spreading means.

It has proven to be particularly expedient to design and/or to arrange the anchor portions resiliently, in particular in such a way that they are forced to counteract a spreading force, that is to say to spring radially inwardly. In accordance with a development, it can thus be ensured very easily from a constructional point of view that the anchor portions return to their unspread position with corresponding actuation of the spreading means so as to thus be removed in a facilitated manner due to the resultant reduction in diameter.

As already mentioned, it is particularly expedient if the spreading means comprise a spindle drive, with which the anchor portions can be spread apart, wherein it is particularly preferable if a spindle of the spindle drive extends in the direction of the longitudinal axis of the subtalar implant. Other spreading mechanisms, such as a wedge drive, and/or a telescopic drive arranged transverse to the longitudinal extension, etc., can be implemented alternatively.

In the preferred embodiment of the spreading means as a spindle drive, it is advantageous if the spindle of the spindle drive is mounted rotatably, in particular in a base portion, which is optionally provided. The spindle preferably comprises, to the rear, a drive, for example an inbus or torx drive, with which the spindle can be rotated relative to the anchor portions, wherein, by rotating the spindle, a spreading slide engaged with the spindle is adjustable along the longitudinal axis of the spindle. The spreading slide preferably engages via an inner thread in an outer spindle thread. An embodiment with a rigid spindle, wherein the spindle slide has to be arranged rotatably, is also conceivable. If a rotatable spindle is provided, the spreading slide is preferably supported non-rotationally at the inner circumference of the anchor portions.

In view of the embodiment of an easily sterilisable spindle that is secured axially by means of a simple construction, it has proven to be advantageous if said spindle is received by means of a thickened portion in a cavity in the subtalar implant, the cavity preferably being formed, at least over portions, by a base portion, which is optionally provided. It is most preferable if a front edge of the base portion is flanged once the spindle has been slid in axially, and thus fixes said spindle. In this case, the axial securing simultaneously forms a sliding bearing for rotatably mounting the spindle.

For facilitated implantation of the proposed subtalar implant, it has proven to be advantageous if an anti-twist mechanism, in particular in the form of lateral recesses, is provided on the spreading slide so as to cooperate with corresponding protrusions of an implantation tool so that unintentional rotation of the subtalar implant when the spindle drive is rotated is reliably prevented. At the same time, a torque can be applied via the anti-twist mechanism so as to screw in the subtalar implant, in particular if an outer thread on the anchor portions is provided between two bones. In any case, the anti-twist mechanism should reliably prevent a relative rotation between the subtalar implant and between the anchor portions of the subtalar implant and the implantation tool.

In a development of the invention, so as to arrange the subtalar implant in the body so as to be secured against rotation in the long-term, a longitudinal groove is provided as an anti-rotation mechanism in at least one of the anchor portions, the longitudinal groove preferably being open to the rear, that is to say against the direction of insertion. Bone material may penetrate the longitudinal groove, and in particular may grow in said groove and may thus contribute to the anti-twist effect.

It is particularly expedient if the subtalar implant can be spread at least by an amount such that the maximum (changeable) diameter thereof can be changed by at least 2 mm, more preferably by more than 3 mm or by approximately 3 mm. The (variable) maximum diameter is preferably selected from a value range between 5 mm and 20 mm, preferably between 10 mm and 16 mm. It is most preferable if at least two different subtalar implants are combined in an implant assortment, wherein a first of the implants is variable in a first diameter range and a second of the implants is variable in a second diameter range, wherein the diameter ranges may overlap, or alternatively may not overlap. For example, it is thus possible and preferable to design an implant such that the maximum diameter thereof is adjustable between 10 mm and 13 mm. In addition or alternatively, an implant may be provided in an implant assortment of which the maximum diameter is to be adjusted in a range between 13 mm and 16 mm.

So as to be able to remove the subtalar implant again during the course of a subsequent operation, the maximum outer diameter of the subtalar implant can preferably be reduced in accordance with a development of the invention, in particular as a result of a corresponding actuation of the spreading means against the direction of rotation during the implantation process. It is most preferable if the anchor portions are radially inwardly resilient so that they automatically tend to move in the direction of their original position, without being urged mechanically.

BRIEF DESCRIPTION OF THE DRAWINGS

Further advantages, features and details of the invention will emerge from the following description of preferred exemplary embodiments and from the drawings, in which:

FIGS. 1a to 1e show different views of a preferred exemplary embodiment of a subtalar implant in an unexpanded state, and, FIGS. 2a to 2d show different views of the subtalar implant according to FIGS. 1a to 1e above in the spread-apart state.

In the figures, like elements and functionally like elements are denoted by like reference signs.

A subtalar implant is illustrated in FIGS. 1a to 1d in the unspread state, wherein a sectional illustration along the line of section A-A according to FIG. 1a is shown in FIG. 1e.

DETAILED DESCRIPTION

The three-part subtalar implant 1 comprises a first anchor portion 2, a diametrically opposed second anchor portion 3 and a (front) base portion 4 formed integrally with the anchor portions 2, 3, wherein the anchor portions 2, 3 and the base portion 4 form a type of sleeve or housing, which is to be considered as a first of the three components of the subtalar implant. The subtalar implant further comprises spreading means 5, which are formed in two parts and consist, in this specific exemplary embodiment, of a rotatably mounted spindle 6, which is provided in some portions with an outer thread 7, and of a spreading slide 8, which is engaged via an inner thread 9 with the outer thread 7 (spindle thread) of the spindle 6. The spindle 6 is provided at its rear end with a drive 10, which is designed in the exemplary embodiment shown as an external hexagon, merely by way of example. By turning the drive 10, the spreading slide 8 can travel relative to the anchor portions 2, along a longitudinal axis L, and in doing so the anchor portions 2, 3 move relative to one another and are supported directly at the spreading slide 8 radially inwardly.

It can be seen in the exemplary embodiment shown that the anchor portions 2, 3 have a slightly conical sleeve contour, even when not spread apart, that is to say in the position in which they are drawn together, although the arrangement may alternatively also be contoured cylindrically, at least in the illustrated unspread state, wherein the embodiment shown has the advantage that anchoring in the respective bone in the foot is also possible in the unspread state.

Both anchor portions 2, 3 extend merely over a circumferential portion of the subtalar implant, in each case by an angle at the circumference of 90° in the exemplary embodiment shown. The anchor portions 2, 3 are provided at their outer circumference with a surface structure 11 (anchoring structure), wherein the surface structures 11 of both anchor portions 2, 3 are part of a common outer thread in the exemplary embodiment shown, that is to say they have a pitch so as to enable the subtalar implant 1 to be anchored in the bone by means of rotation. Alternatively, the pitch can also be omitted for example and a grooved structure can be provided, or alternatively another anchoring structure. It must be ensured, however, that the anchor portions 2, 3 can be anchored in the bone.

It can be seen from FIG. 1d that a longitudinal groove 12 that is open to the rear is provided in each of the anchor portions 2, 3 and, in the implanted state, serves as an anti-twist mechanism. Alternatively, a plurality of longitudinal grooves, which are parallel for example, may also be provided in at least one anchor portion to improve the anti-twist effect.

It can be seen from FIG. 1e (longitudinal sectional view) that the spindle 6 can be assembled from a front end 13 of the implant 1, wherein the spindle 6 can be slid in the direction of a rear end 14 of the implant 1 into a spindle seat 15 defined by the base portion 4 and the anchor portions 2, 3. In a front region of the base portion 4, a cavity 16 is formed, in which a thickened front portion 17 (enlarged diameter portion) of the spindle 6 can be received. By flanging a front circumferential edge 18 of the base portion 4, the spindle 6 can be secured axially to the front. The thickened portion 17 is supported axially to the rear at an inner annular shoulder 18 of the cavity 16. As can be seen clearly from the drawings, the subtalar implant 1 (for reasons of clarity) is not yet assembled in the final position—the circumferential edge 18 still needs to be flanged.

The anchor portions 2, 3 are resilient. To illustrate the resilience, a gap 20 is indicated in FIG. 2a, which is not provided in reality—in this case there is no expansion, just elastic deformation. The resilience of the anchor portions 2, 3, which are forced to spring radially inwardly in the direction of the longitudinal central axis L, can be selected by matching the material thickness in a transition region 21 between the circumferentially closed base portion 4 and the actual surface-structured anchor portions 2, 3 and by influencing the geometry of the transition portion, for example by selection of the radius of curvature of a lateral depression 22.

It can be seen from FIG. 1a that two mutually opposed lateral recesses 23, which are concavely contoured in this instance and extend in the longitudinal direction, are provided on the spreading slide 8, which is contoured in cross section in a substantially rectangular manner, a corresponding implantation tool (not illustrated) being capable of engaging in said recesses so as to prevent rotation of the spreading slide 8, and therefore also of the anchor portions 2, 3, relative to the implantation tool, in particular if the drive 10 is actuated by an implantation tool. By means of the recesses 23, a torque can also be applied to the subtalar implant 1 by means of the implantation tool so as to facilitate anchoring in the bone.

It can also be seen in FIG. 1b that the spreading slide does not exceed, radially outwardly, a virtual circle defined over portions by the anchor portions 2, 3, so that the spreading slide 8 does not hinder a possible desired rotation of the subtalar implant 1 by means of an implantation tool.

It can be seen from FIG. 1e that the spindle 6 is penetrated by a continuous channel 24, which can be used to receive a Kirschner wire and/or an axial extension of a possible implantation tool.

In FIGS. 2a to 2d, the subtalar implant 1 is shown in a spread-apart position. This has been set by actuating the drive 10 and thus rotating the spindle 6, whereby the spreading slide 8 is consequently moved to the left in the drawing plane, that is to say in the direction of the front end 13 of the subtalar implant 1, and the anchor portions 2, 3 are thus expanded, that is to say adjusted radially based on the longitudinal central axis L, whereby a cone angle (angle changes between two diametrically opposed lateral surface portions of the conical sleeve contour 25) has enlarged in this instance.

The subtalar implant 1 shown in the figures can be adjusted between an outer diameter a1 indicated in FIG. 1a of 10 mm up to an outer diameter a2 indicated in FIG. 2a of 13 mm.

The invention claimed is:

1. A subtalar implant for stabilising the subtalar joint in the human foot, comprising a longitudinal axis extending between a front end and a rear end, comprising a first anchor portion arranged on a first side of the longitudinal axis and a second anchor portion arranged on a second side of the longitudinal axis, the second side opposite to the first side,
   and further comprising spreading means for spreading apart the implant at the rear end as a result of relative displacement of the first and second anchor portions,
   wherein the spreading means comprise a spindle drive, the spindle drive comprising a rotatably mounted spindle having a proximal end adjacent to the front end of the implant and a distal end adjacent to the rear end of the implant, a drive interface, and a spreading slide being adjustable along the longitudinal axis by rotating said spindle, wherein the spreading slide and the drive interface are disposed closer to the rear end of the implant than the front end of the implant, and wherein the drive interface faces toward and is accessible from the rear end of the implant, the drive interface configured to receive an instrument to drive rotation of the spindle.

2. The subtalar implant according to claim 1, wherein the anchor portions extend from a base portion, the anchor portions and the base portion together forming a sleeve having a sleeve contour, and wherein an angle of spread, which is spanned by the anchor portions of the sleeve contour can be set in stages or continuously by actuation of the spreading means.

3. The subtalar implant according to claim 2, wherein the sleeve contour is conical.

4. The subtalar implant according to claim 1, wherein the anchor portions are diametrically opposed.

5. The subtalar implant according to claim 4, further comprising at least a third anchor portion, wherein the anchor portions are uniformly spaced around a circumference of the implant.

6. The subtalar implant according to claim 1, wherein the front and the rear end are connected via a continuous channel for receiving a Kirschner wire.

7. The subtalar implant according to claim 1, each anchor portion having an outer surface including at least one thread or at least one groove.

8. The subtalar implant according to claim 7, wherein the outer surface of each anchor portion includes a plurality of grooves arranged in succession along the longitudinal axis of the implant.

9. The subtalar implant according to claim 1, wherein the anchor portions are formed integrally with a base portion.

10. The subtalar implant according to claim 9, wherein the base portion includes an inner cavity, and wherein an enlarged end portion of the spindle is configured to be received within the cavity to axially secure the spindle to the front end.

11. The subtalar implant according to claim 10, wherein the spindle is rotatable within the cavity.

12. The subtalar implant according to claim 1, wherein the anchor portions are biased in a direction radially inward toward the longitudinal axis.

13. The subtalar implant according to claim 1, wherein at least one longitudinal groove is formed as an anti-rotation mechanism in at least one of the anchor portions.

14. The subtalar implant according to claim 1, wherein a maximum diameter of the implant can be changed by an amount of at least 2 mm, the diameter being selected from a value range between 5 mm and 20 mm.

15. The subtalar implant according to claim 14, wherein the value range is between 10 mm and 16 mm.

* * * * *